(12) United States Patent
Tanga et al.

(10) Patent No.: US 6,607,908 B1
(45) Date of Patent: Aug. 19, 2003

(54) SUPPORTS FOR IMMOBILIZING DNA OR THE LIKE

(75) Inventors: Michifumi Tanga, Yamaguchi-ken (JP); Kojiro Takahashi, Hiroshima-ken (JP)

(73) Assignee: Toyo Kohan Co., Ltd., Tokyo (JP)

( * ) Notice: Subject to any disclaimer, the term of this patent is extended or adjusted under 35 U.S.C. 154(b) by 0 days.

(21) Appl. No.: 09/807,611

(22) PCT Filed: Oct. 15, 1999

(86) PCT No.: PCT/JP99/05712

§ 371 (c)(1),
(2), (4) Date: Jul. 16, 2001

(87) PCT Pub. No.: WO00/22108

PCT Pub. Date: Apr. 20, 2000

(30) Foreign Application Priority Data

Oct. 15, 1998 (JP) .......................................... 10-293480

(51) Int. Cl.[7] .......................... C12M 1/34; C12Q 1/68; C12P 19/34; C07H 21/02; C07H 21/04

(52) U.S. Cl. ........................ 435/287.2; 435/6; 435/7.1; 435/91.1; 435/91.2; 536/22.1; 536/23.1; 536/24.3; 536/24.31; 536/24.32; 536/27.33

(58) Field of Search ............................ 435/6, 7.1, 91.1, 435/91.2, 287.2; 536/22.1, 23.1, 24.3–24.33

(56) References Cited

U.S. PATENT DOCUMENTS

| 5,252,724 A | | 10/1993 | Kishimoto et al. | |
|---|---|---|---|---|
| 5,607,560 A | * | 3/1997 | Hirabayashi et al. | 207/192.15 |
| 5,679,269 A | * | 10/1997 | Cohen et al. | 216/72 |
| 5,730,940 A | * | 3/1998 | Nakagawa | 422/68.1 |
| 6,133,436 A | * | 10/2000 | Koster et al. | 536/24.3 |
| 6,297,008 B1 | * | 10/2001 | Okamoto et al. | 435/6 |

OTHER PUBLICATIONS

Abstract of JP 62–079784 A, Apr. 13, 1987, Dialog.
Abstract of JP 04–228075 A, Aug. 18, 1992, Dialog.

* cited by examiner

Primary Examiner—Jeffrey Siew
(74) Attorney, Agent, or Firm—Browdy and Neimark PLLC

(57) ABSTRACT

A subject of the present invention is to provide a support with immobilized DNA as a DNA library and particularly to a support suitable for reproducing DNA in accordance with a DNA amplification reaction. In the present invention, DNA or the like is immobilized on a surface of a support made of one kind or more than material Selected from a group of a diamond including non-diamond carbon, amorphous carbon and graphite. A hydroxyl group may be bonded to a surface of the support or a group bonded to a hydrocarbon group and a carboxyl group at its terminal end may be bonded to a surface of the support through an ester linkage or a peptide linkage.

7 Claims, No Drawings

SUPPORTS FOR IMMOBILIZING DNA OR THE LIKE

REFERENCE TO RELATED APPLICATIONS

The present application is the national stage under 35 U.S.C. §371 of international application PCT/JP99/05712, filed Oct. 15, 1999, which designated the United States, and which application was not published in the English language.

INDUSTRIAL FIELD

The present invention relates to supports for immobilizing DNA or the like, particularly to supports which are chemically modified, more particularly to supports which are chemically modified by a hydroxyl group, a carboxyl group and so on at the terminal thereof.

BACKGROUND OF THE INVENTION

In a conventional process, in order to obtain a specific amount of target DNA, the following heat cycle 1) to 3) has to be repeated in a DNA amplification reaction and so on:

1) the temperature of a test material is increased to 95° C. in order to break the hydrogen bonds of the double chain;
2) the temperature of the test material is decreased to 45° C. in order to reproduce DNA by adding a primer; and
3) the temperature of the test material is increased to 74° C. in order to reproduce DNA by extending the primer with heat-resistant polymerase.

In such a DNA amplificaiton reaction, the test material is filled into a container made from synthetic resin. The container is installed in an aluminum block and heat-cycled.

However, it requires many hours to accomplish the heat cycle. It requires several hours to obtain a target amount of DNA. There is a drawback that others kinds of DNA are also reproduced in addition to the target DNA since the accuracy of thermal control is low.

To resolve the above drawback, a subject of the present invention is to provide a support suitable for immobilizing DNA easily and reproducing DNA by a DNA amplification reaction.

DISCLOSURE OF THE INVENTION

A support according to the present invention is comprises at least one component selected from the group of diamond, including non-diamond carbon, amorphous carbon, and graphite.

The support preferably has a chemical modification such as polar group, hydroxyl group or carboxyl group at its terminal.

The carboxyl group is preferably linked to a surface of the support through an ester linkage or a peptide linkage.

BEST MODE FOR CARRYING OUT THE INVENTION

Regarding carbon material such as diamond including non-diamond carbon, amorphous carbon and graphite and so on, carbons are exposed on a surface of the support so that the surface can be chemically modified with a hydroxyl group, a carboxyl group and so on and DNA and so on can be immobilized easily. It is the most suitable to reproduce DNA and so on by a DNA amplification reaction.

Even if a surface of the support according to the present invention is contaminated, chemical modification can be reproduced by hydrolyzing.

The support according to the present invention comprises diamond including non-diamond carbon, amorphous carbon, graphite and so on. Although any methods for producing the surface can be used, a microwave plasma CVD method, an ECR CVD method, a high frequency plasma CVD method, an IPC method, a DC sputtering method, an ECR sputtering method, an ion plating method, an arc ion plating method, an EB evaporation method, a resistance heating evaporation method and so on are preferable. For example, carbon may be amorphous carbon with hydrogen obtained by steam-baking a resist layer made of polyimide material. Further, carbon may be sintered slurrying resin mixed with graphite powder. In the present invention, carbon may be selected from one or more than materials described above.

A surface of the support according to the present invention may be roughened. Such a rough surface has a relatively large surface area on which a large amount of DNA can be immobilized. The shape of the support may be a plate shape, a ball shape, polygon shape or various shapes. The material of the support may be mixed with the above described material and the other components. The support according to the present invention may be exposed on a surface of an object.

In the next, a specific group is chemically modified (added) on a surface of the above support. By providing a chemical modification, DNA is able to be immobilized on the surface of the support. A hydroxyl group, a carboxyl group, a surface group, a cyano group, a nitro group, a thiol group, an amino group and so on may be utilized as a specific group having a polar group and chemically modified on a surface of the support. In addition, an organic carbonic acid is also available.

The carboxyl group may be bonded to a terminal of the support through the other hydrocarbon group. In such a case, it is preferable that the number of carbons in the hydrocarbon group is from zero to 10 in order to immobilize DNA. Regarding the acid which can be charged to be a hydrocarbon group, a mono-carboxylic acid such as formic acid, acetic acid, propionic acid, di-carboxylic acid such as oxalic acid, malonic acid, succinic acid, maleinic acid, fumaric acid, phthalic acid and a polycarboxylic acid such as trimellitic acid are considerable.

In the case of utilizing the support according to the present invention for a DNA amplification reaction, there are two options, that is, one option is to require a hydrolysis-resist characteristic and another option is to require a reproduction of chemical modification by hydrolyzing.

In the case of requiring the hydrolysis-resist characteristic, it is preferable that a carboxyl group bonded to a terminal end of the hydro-carbon group is bonded to a surface of the support through a peptide linkage in order to provide alkali-proof characteristic.

On the other hand, in the case of requiring a reproduction of chemical modification by hydrolyzing and removing the produced chemical modification, it is preferable that a carboxyl group bonded to a terminal end of the hydro-carbon group is bonded to a surface of the support through an ester linkage.

Regarding a method for bonding a hydroxyl group to a terminal end of a hydro-carbon group on the surface of the support, a method for oxidizing a surface of the support with oxygen plasma and treating with steam, a method for chloridizing a surface of the support by irradiating ultra violet beam in chloride gas and hydrolyzing the support by hydrolyzing in alkali solution are suitable.

Methods for linking the carboxyl group bonded to the terminal end of the hydro-carbon group on the surface of the support through the peptide linkage, include chloridizing a surface of the support by irradiating with ultra violet radiation in chloride gas, aminatizing the support by irradiating with ultra violet radiation in ammonia gas, reacting with carbonic chloride in a non-water soluble solution and neutralizing in alkaline solution.

Methods for bonding the carboxyl group connected to a terminal end of the hydrocarbon group on a surface of the support through an ester linkage, include chloridizing the surface of the support by irradiating with ultra violet radiation in chloride gas, reacting with sodium carbonate in non-water soluble solution and neutralizing in a weak acid solution and a oxidizing a surface of the support with oxygen plasma, chloridizing, hydrolyzing by hydrolyzing in alkali solution, reacting with carbonic chloride in non-water soluble solution and neutralizing in alkaline solution.

EXAMPLES

Examples according to the present invention will be described in detail hereinafter.

Example 1

A diamond circular plate including non-diamond carbon of which a diameter is 64 mm, a thickness is 0.1 mm and a surface roughness Ra is 0.5 mm is vapor-phased by a microwave plasma CVD method. Regarding a peak ratio of non-diamond carbon (uncompleted diamond) with respect to diamond carbon (completed diamond), an area of 10 mm×10 mm of the circular plate is analyzed by Raman spectroscopic analysis method so that an existence of non-diamond carbon can be recognized. A test piece including the non-diamond carbon of 10 mm×10 mm is cut off from the circular plate.

In the example 1, after the surface of the test piece is oxidized with oxygen plasma energized by microwave, the test piece is set in a separable flask. After instituting atmosphere in the flask with steam, the atmosphere is heated at 400° C. for 30 minutes while steam is added to the flask. After the test piece is cooled, the test piece is picked up and dried so as to obtain a support having a hydroxyl group at its terminal end.

In accordance with a SIMS method, the test piece is cut off and treated with oxygen plasma and steam in order. Then, each peak strength of hydrogen and hydroxyl group is measured, respectively. In the case of the peak strength of hydrogen as 1, the peak strength ratio of the hydroxyl group is as follows.

|  | Peak strength ratio of hydroxyl group |
| --- | --- |
| After cutting off test piece | 0.11 |
| After treating with oxygen plasma | 0.61 |
| After treating with steam | 1.09 |

As shown in the above table, the peak strength ratio of the hydroxyl group is increased by processing the oxygen plasma a treatment, the steam treatment. Therefore, it can be recognized that a surface of the support is chemically modified by a hydroxyl group.

Example 2

A diamond circular plate including non-diamond carbon of which a diameter is 64 mm, a thickness is 0.1 mm and a surface roughness Ra is 0.3 mm is vapor-phased by a microwave plasma CVD method. An area of 10 mm×10 mm of the circular plate is analyzed by Raman spectroscopic analysis method. As the result, all the carbon are non-diamond carbon (uncomplicated diamond). A test piece of 10 mm×10 mm is cut off from the circular plate by laser beam.

The test piece is set in a separable flask. After flushing the flask with argon gas, the test piece is irradiated by ultra violet beams produced by a Hg—Xe lamp of which a main wavelength is 3600 Å for 60 minutes in order to chloridize a surface of the test piece while chloride gas is introduced into the flask per 1SCCM. After flushing the atmosphere with argon gas, the test piece is picked up. The test piece is boiled is sodium hydroxide solution of 10 wt % for 15 minutes. After washing with water and drying, a support having a hydroxyl group at a terminal end is obtained.

In accordance with the SIMS method, each peak strength of hydrogen, the hydroxyl group and the chloride group is measured at a timing before chloridizing, a timing after chloridizing and a timing after treating with sodium hydroxide in order. In the case of the peak strength of hydrogen as 1, the peak strength ratio of the hydroxyl group and the chloride group are as follows.

|  | Peak strength ratio | |
| --- | --- | --- |
|  | Hydroxyl group | Chloride group |
| Before chloridizing | 0.11 | — |
| After chloridizing | 0.17 | 0.47 |
| After treating with sodium hydroxide | 0.45 | 0.31 |

As described above, the peak strength ratio of the hydroxyl group is gradually increased by conducting the chloridizing treatment and the sodium hydroxide treatment. Thus, it is recognized that a surface of the support is chemically modified with the hydroxyl group. Judging from decreasing the ratio of the chloride group, it is recognized that the chloride group is instituted to the hydroxyl group.

Example 3

A diamond circular plate including complete diamond carbon and non-diamond carbon having a diameter of 64 mm, a thickness of 0.1 mm and a surface roughness Ra of 0.5 mm is vapor-phased by a microwave plasma CVD method. Regarding a peak ratio of non-diamond carbon (uncompleted diamond) with respect to diamond carbon (completed diamond), an area of 10 mm×10 mm of the circular plate is analyzed by the Raman spectroscopic analysis method so that an existence of non-diamond carbon can be recognized. A test piece including the non-diamond carbon of 10 mm×10 mm is cut off from the circular plate. After oxidizing a surface of the test piece with oxygen plasma energized by microwave, a surface of the test piece is chloridized. After flushing atmosphere with argon gas, the test piece is picked up. The test piece is boiled in sodium hydroxide solution of 10 wt % for 15 minutes. After being cleaned with water and dried, a support having a hydroxyl group at its terminal end is obtained.

In accordance with the SIMS method, after polishing a surface of the test piece, each peak strength of hydrogen, the hydroxyl group and the chloride group is measured at a timing before oxygen plasma treatment, a timing after oxygen plasma treatment, a timing after chloridizing and a timing after sodium hydroxide treatment in order.

|  | Peak strength ratio | |
| --- | --- | --- |
|  | Hydroxyl group | Chloride group |
| Before oxygen plasma treatment | 0.11 | — |
| After oxygen plasma treatment | 0.67 | — |
| Chloridizing | 0.19 | 0.44 |
| sodium hydroxide treatment | 0.50 | 0.30 |

As shown in the above Table, the peak strength ratio of the hydroxyl group is gradually increased by passing the oxygen plasma treatment, chloridizing and sodium hydroxide so that it can be recognized a surface of the support is chemically modified with the hydroxyl groups. Judging from decreasing the chloride group, it is recognized that the chloride is instituted with the hydroxyl group.

Example 4

A graphite circular plate is formed by a sputtering method. A test piece of 10 mm×10 mm is cut off from the circular plate by laser beam. The test piece is set in a separable flask. After flushing the atmosphere in the flask with argon gas, the test piece is irradiated by ultra violet beams produced by a Hg—Xe lamp of which a main wavelength is 3600 Å for 60 minutes in order to chloridize a surface of the test piece while chloride gas is introduced into the flask per 1SCCM. After adding argon gas to the atmosphere in the flask again, N-dimethyl formamide solution of 100 ml of sodium salt of sebacic acid of 1 wt % is added. A condenser is provided at the separable flask and refluxed for two hours. Then, the test piece is picked up. After cleaning the test piece with acetic acid solution of 1 wt %, the test piece is further cleaned with acetone and dried. Thus is obtained a support having a carboxyl group linked with the sebacic acid through an ester linkage at a terminal.

In accordance with the SIMS method, each peak strength of hydrogen, hydroxyl group and the chloride group is measured at a timing before chloridizing, a timing after chloridizing and a timing after sebacic soda treatment in order. In the case of the peak strength of hydrogen as 1, the peak strength ratio of the hydroxyl group and the chloride group are as follows.

|  | Peak strength ratio | |
| --- | --- | --- |
|  | Hydroxyl group | Chloride group |
| Before chloridizing | 0.11 | — |
| After chloridizing | 0.17 | 0.47 |
| Sebacic soda treatment | 0.35 | 0.31 |

As shown in the above Table, the peak strength ratio of the hydroxyl group is gradually increased by passing the chloridizing treatment and the successive sodium salt of sebacic acid treatment. In accordance with the FTIR method, absorption strength caused by stretching vibration between carbon and hydrogen on a surface of the test piece and absorption strength caused by stretching vibration between carbon and oxygen are measured. The absorption strength of the both cases are increased (an increasing ratio of the absorption strength with respect to a surface blank of the test piece is about 30%). Judging from the fact, it is recognized that the surface of the support is chemically modified by a group bonded to the carboxyl group at its terminal end of hydrocarbon group of the sebacic acid. The chloride group is decreased so that it can be recognized the chloride group is instituted with the hydroxyl group.

Example 5

A resist layer made from polyimide system material is baked with steam so as to form a thin plate made from amorphous carbon including hydrogen. A test piece of 10 mm×10 mm is cut off from the thin plate by laser beam. After oxidizing a surface of the test piece with oxygen plasma energized by microwave, a surface of the test piece is chloridized. After flushing the atmosphere with argon gas, the test piece is picked up. The test piece is boiled in potassium hydroxide solution of 10 wt % for 15 minutes so as to modify the surface of the test piece with hydroxyl group. After drying the test piece, the test piece is set in a separable flask with a condenser with a calcium chloride dry tube provided at an upper portion of the separable flask. Chloroform of 50 ml and triethylamine of 1 g are added and the atmosphere in the separable flask is flushed with argon gas. While the separable flask is cooled with ice, chloroform solution of 50 ml in which 10 g of succinyl chloride is dissolved is gradually added. After refluxing for four hours, the test piece is picked up. The test piece is cleaned with potassium carbonate solution of 10 wt % and then cleaned with acetone. After drying the test piece, there is obtained a support having a carboxyl group bonded to malonic acid through an ester linkage at its terminal end.

In accordance with a SIMS method, each peak strength of hydrogen and hydroxyl group is measured at a timing before oxygen plasma treatment, a timing after oxygen plasma treatment, a timing after chloridizing, a timing after hydrolyzing and a timing after succinyl chloride treatment in order. In the case of the peak strength of hydrogen as 1, the peak strength ratio of the hydroxyl group is as follows.

|  | Peak strength ratio of hydroxyl group |
| --- | --- |
| Before oxygen plasma treatment | 0.11 |
| After oxygen plasma treatment | 0.66 |
| After chloridizing | 0.19 |
| After hydrolyzing | 0.65 |
| After succinyl chloride treatment | 0.46 |

As shown in the above Table, the peak strength ratio of the hydroxyl group is gradually increased by passing the oxygen plasma treatment, the chloridizing treatment, the hydrolyzing treatment and the succinyl chloride treatment. In accordance with the FTIR method, absorption strength caused by stretching vibration between carbon and hydrogen on a surface of the test piece and absorption strength caused by stretching vibration between carbon and oxygen are measured. The absorption strength of the both cases are increased (an increasing ratio of the absorption strength with respect to a surface blank of the test piece is about 25%). Judging from the fact, it is recognized that a surface of the support is chemically modified by a group bonded to the carboxyl group at its terminal end of hydrocarbon group of the malonic acid.

Example 6

A graphite circular plate having a diameter of 64 mm, a thickness of 0.1 mm and a surface roughness Ra of 0.3 mm is vapor-phased by vaporizing slurry type solvent mixed with graphite powder and resin powder. In the circular plate, an area of 10 mm×10 mm of the circular plate is analyzed by Raman spectroscopic analysis method so that all of the diamond carbon are non-diamond carbon (amorphous carbon). A test piece of 10 mm×10 mm is cut off from the circular plate. After hydrogenating a surface of the test piece by hydrogen plasma energized by microwave, the surface of the test piece is chloridized. After setting the test piece in a separable flask, the atmosphere in the separable flask is flushed with argon gas. While ammonia gas is introduced to the flask per 1SCCM, the surface of the test piece is aminated by irradiating ultra violet of which a main wavelength is 3600 Å produced by a Hg—Xe lamp for 60 minutes. After flushing the atmosphere with argon gas, a condenser with a chloride calcium dry tube is provided at an upper portion of the separable flask. Chloroform of 50 ml is added and the atmosphere is flushed with argon gas.

While the separable flask is cooled with ice, chloroform solution of 50 ml mixed with succinyl chloride of 10 g is gradually added. After refluxing for 4 hours, the test piece is picked up and cleaned with potassium carbonate solution of 10 wt %. The test piece is further cleaned with acetone and dried so that a support having the carboxyl group bonded to malonic acid through a peptide linkage at its terminal end can be obtained.

In accordance with the SIMS method, each peak strength of hydrogen, hydroxyl group and chloride group is measured at a timing before chloridizing, a timing after chloridizing, a timing of succinyl chloride treatment in order. In the case of the peak strength of hydrogen as 1, the peak strength of the hydroxyl group and the chloride group are shown as follows.

| | Peak strength ratio | |
| --- | --- | --- |
| | Hydroxyl group | Chloride group |
| Before chloridizing | 0.11 | — |
| After chloridizing | 0.19 | 0.45 |
| After aminating | 0.16 | 0.10 |
| After succinyl chloride treatment | 0.55 | 0.10 |

As shown in the above Table, the peak strength ratio of the hydroxyl group increases step by step by passing the hydrogen plasma treatment, the successive chloridizing treatment, the hydrolyzing treatment and the succinyl chloride treatment. In accordance with the FTIR method, absorption strength caused by stretching vibration between carbon and hydrogen on a surface of the test piece and absorption strength caused by stretching vibration between carbon and oxygen are measured. The absorption strength of the both cases are increased (an increasing ratio of the absorption strength with respect to a surface blank of the test piece is about 25%).

Judging from the fact, it is recognized that a surface of the support is chemically modified by a group bonded to the carboxyl group at a terminal end of hydroxide group of the malonic acid.

A DNA amplification reaction is operated on supports chemically modified with the carboxyl group at the terminal end as described in the examples 1 to 6, and a target amount of DNA can be obtained within 1 hour.

By utilizing a support chemically modified according to the present invention, a terminal end of the oligonucleotide is immobilized to a hydroxyl group or a carboxyl group a its terminal through a hydrogen linkage. Further DNA having complementary base sequence with respect to the oligonucleotide is immobilized so as to use as a DNA library chip. Instead of DNA, nucleotide, oligonucleotide, DNA fragment and so on can be immobilized on a surface of a diamond support as a library.

POSSIBILITY OF USE IN THE INVENTION

A support according to the present invention comprises carbon material so that DNA can be immobilized easily on the support and a DNA amplification reaction is operated very easily.

In the support according to the present invention, a surface of the support is chemically modified with a hydroxyl group or a carboxyl group and so on so that an immobilization of DNA and so on can become stable and the support can be utilized as a chip for reproducing DNA by the DNA amplification reaction.

Even if a surface of the support according to the present invention is contaminated, the chemical modification can be reproduced by hydrolysis. A production cost of a DNA chip can be saved.

What is claimed is:

1. A support for immobilizing DNA comprising at least one material selected from the group consisting of diamond, uncompleted diamond, and amorphous carbon, wherein said material is produced by microwave plasma CVD, ECR CVD, high frequency plasma CVD, IPC, DC sputtering, ECR sputtering, ion plating, arc ion plating, EB evaporation, or resistance heating evaporation, said support being chemically modified by a polar group bonded to the surface of the support such that DNA is immobilized thereon.

2. The support according to claim 1 wherein a hydroxyl group, a sulfate group, a cyano group, a nitro group, a thiol group, an amino group, or a carboxyl group at the surface of the support is bonded to the support.

3. The support according to claim 2 wherein the support is chemically modified by a carboxyl group, and the carboxyl group is bonded to a surface of said support through an ester linkage containing a hydrocarbon chain having from 1 to 10 carbon atoms.

4. The support according to claim 2 wherein the support is chemically modified by a carboxyl group and the carboxyl group is bonded to the surface of the support through a peptide linkage.

5. The support according to claim 1 wherein the DNA is immobilized on the support through a hydrogen linkage at a terminal end of a hydroxyl group on the support or through a carboxyl group of an oligonucleotide.

6. The support according to claim 1 and wherein a hydroxal group is bonded to the surface of the support for immobilizing DNA thereon.

7. The support according to claim 2 wherein a hydroxyl group is bonded to the surface of the support.

\* \* \* \* \*